US012774271B2

(12) United States Patent
Sui

(10) Patent No.: US 12,774,271 B2
(45) Date of Patent: Oct. 27, 2026

(54) PROCESS FOR THE PRODUCTION OF LACTIDE

(71) Applicant: POLYWIN PTE. LTD., Singapore (SG)

(72) Inventor: Jianjun Sui, Singapore (SG)

(73) Assignee: POLYWIN PTE. LTD., Singapore (SG)

( * ) Notice: Subject to any disclaimer, the term of this patent is extended or adjusted under 35 U.S.C. 154(b) by 454 days.

(21) Appl. No.: 18/259,104

(22) PCT Filed: Dec. 24, 2020

(86) PCT No.: PCT/SG2020/050779
§ 371 (c)(1),
(2) Date: Jun. 23, 2023

(87) PCT Pub. No.: WO2022/139675
PCT Pub. Date: Jun. 30, 2022

(65) Prior Publication Data

US 2024/0043397 A1 Feb. 8, 2024

(51) Int. Cl.
*C07D 319/12* (2006.01)

(52) U.S. Cl.
CPC .................................. *C07D 319/12* (2013.01)

(58) Field of Classification Search
None
See application file for complete search history.

(56) References Cited

U.S. PATENT DOCUMENTS 8,053,584 B2 * 11/2011 Meerdink ............ C07D 319/12 203/99
10,058,795 B2 * 8/2018 Stepanski ................ B01D 3/02
2010/0099893 A1 4/2010 Scholz et al.
2010/0249362 A1 9/2010 Kamikawa et al.
2010/0249364 A1 * 9/2010 Hagen ...................... B01D 3/14 528/307

FOREIGN PATENT DOCUMENTS

| | | | |
|---|---|---|---|
| CN | 101696203 | A | 4/2010 |
| CN | 102675103 | A | 9/2012 |
| CN | 103442776 | A | 12/2013 |
| CN | 211384958 | U | 9/2020 |
| GB | 1428228 | A | 3/1976 |
| WO | 9315127 | A1 | 8/1993 |

OTHER PUBLICATIONS

International Search Report from International Application No. PCT/SG2020/050779 mailed Apr. 1, 2021.

* cited by examiner

*Primary Examiner* — Valerie Rodriguez-Garcia
(74) *Attorney, Agent, or Firm* — Shih IP Law Group, PLLC

(57) ABSTRACT

This invention relates to a process for the continuous production of optically pure lactide from an aqueous solution of lactic acid by means of two reactive distillations followed by a main distillation column with a side-draw refluxer. The first reactive distillation is used for the preparation of lactic acid oligomers and the second reactive distillation used for the depolymerization of the thus obtained lactic acid oligomers to lactide. The crude lactide generated from the second reactive distillation is further purified in the main distillation column with a side-draw refluxer being connected to.

3 Claims, 1 Drawing Sheet

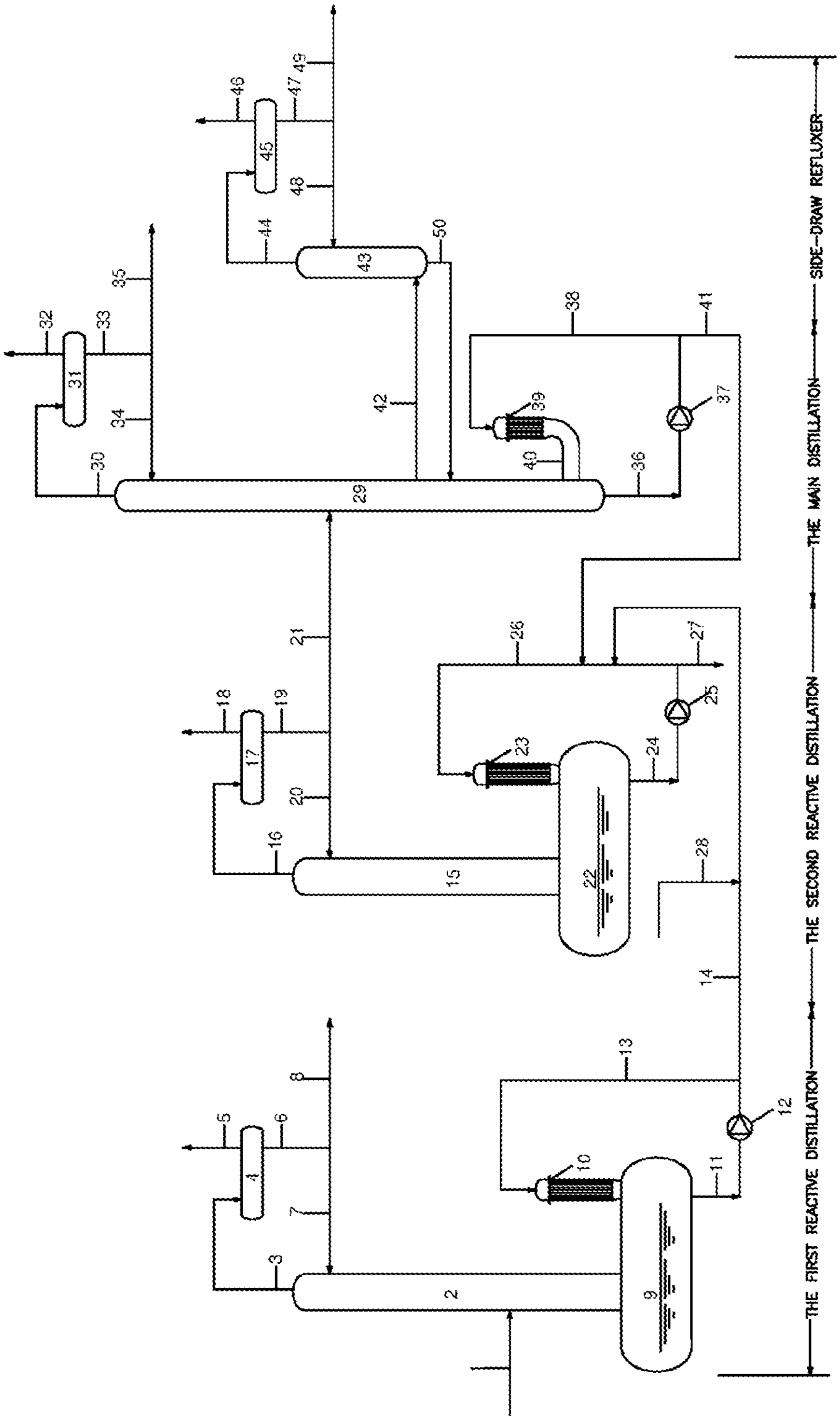
THE FIRST REACTIVE DISTILLATION
THE SECOND REACTIVE DISTILLATION
THE MAIN DISTILLATION
SIDE-DRAW REFLUXER

PROCESS FOR THE PRODUCTION OF LACTIDE

BACKGROUND OF THE INVENTION

This invention relates to a process for the continuous production of optically pure lactide by means of two reactive distillations followed by a main distillation column with a vapor side-draw refluxer being connected to.

Lactides are cyclic dimers of lactic acid and can be used as intermediates in the production of high molecular weight polylactic acid. These polymers may be useful in the biomedical industry and other applications, for example as a decomposable packaging material due to their ability to be degraded biologically and hydrolytically while forming environmentally acceptable degradation products.

Examples of known methods for synthesizing lactide comprise a step of concentrating lactic acid as a raw material to reduce the water content and facilitate the initiation of esterification between lactic acid molecules, a step of pre-polymerizing lactic acid to generate lactic acid oligomers during the removal of water resulting from esterification and a step of depolymerizing the thus obtained lactic acid oligomers to crude lactide. Methods for performing said concentration, pre-polymerization and depolymerization are known in the art, e.g., U.S. Pat. No. 6,326,458.

It is well known in the art that lactic acid includes two optical isomers, i.e., the (R)-lactic acid and (S)-lactic acid. Thus, formation of lactide from the enantiomers of lactic acid gives rise to three stereoisomers with different geometric structures distinguished as (R, R)-lactide (or D-lactide), (S, S)-lactide (or L-lactide) and (R, S)-lactide (or meso-lactide). In practice, a crude lactic acid feed to the system contains one of the two lactic acid selected from (S)-lactic acid and (R)-lactic acid as a major component. Therefore, the crude lactide produced by depolymerization contains a major portion of an optically pure lactide (L-lactide or D-lactide), a minor portion of meso-lactide and the remaining third lactide in an even much smaller amount.

While such a three-step method described in U.S. Pat. No. 6,326,458 allows to obtain crude lactide from an aqueous solution of lactic acid, one disadvantage of the process is the increased exposure of lactic acid to elevated temperatures as it is concentrated and pre-polymerized to the lactic acid oligomers. The starting lactic acid is usually of very high optical purity, with the (S)-lactic acid being more commercially available. However, some racemization occurs under those conditions, e.g., conversion of (S)-lactic acid to (R)-lactic acid, which results in a loss of the main product L-lactide and an increase in the amount of meso-lactide in the crude lactide. This can cause problems during the separation of meso-lactide from the optically pure lactide, for example L-lactide. An additional purification step may be required before the polymerization is performed. Therefore, it would be desirable to provide a more efficient method for minimizing the lactic acid racemization and increasing the yield of L-lactide.

The crude lactide from depolymerization not only comprises lactide but also other impurities, such as residual lactic acid, water, lactic acid oligomers and other reaction byproducts. The molecular weight of polylactic acid is controlled by the amount of hydroxylic impurities in lactide. In particular the presence of water, lactic acid and lactic acid oligomers in lactide tends to retard polymerization, and the resulting polylactic acid will not have a high molecular weight suitable for its use as a biodegradable polymer. It has been shown that the separation of the impurities from L-lactide can be achievable by means of distillation based on volatility differences between components. The relative order of decreasing volatility of the principal components of the crude lactide is water, lactic acid, meso-lactide, L-lactide and linear lactic acid dimers with boiling points at atmospheric pressure of about 100, 215, 250, 255 and 350° C., respectively, which boiling points are even higher for linear lactic acid trimers, tetramers, etc.

As described in U.S. Pat. No. 5,236,560, a crude lactide containing lactide, lactic acid, lactic acid oligomers and water is fed to a distillation column, wherein the purified lactide is withdrawn in the form of vapor from the side-draw of the distillation column.

U.S. Pat. No. 10,023,553 describes a process, wherein the crude lactide prepared by depolymerization is maintained for a period of at least 5 hours in a reaction vessel prior to a distillation column, in a purpose of decreasing the lactic acid content at the cost of increasing the lactic acid oligomers content. The purified lactide in the form of vapor is removed from the side-draw of the distillation column.

While the purified vapor lactide substantially free of lactic acid can be obtained as the side-draw product from the distillation columns described in U.S. Pat. Nos. 5,236,560 and 10,023,553, it still contains a small amount of meso-lactide and lactic acid oligomers. Part of the lactic acid oligomers are formed due to the side reaction of lactic acid with lactide during the distillation. The residual lactic acid oligomers in the purified lactide have a negative impact on the polymerization rates during the polymerization, resulting in a relatively low molecular weight polylactic acid. In order to obtain virtually pure L-lactide, the purified vapor lactide is condensed and is subjected to a further purification step, e.g., melt crystallization. The residual meso-lactide can be easily separated from L-lactide by melt crystallization. However, it is difficult to remove the residual lactic acid oligomers from the lactide by melt crystallization as the lactic acid oligomers tend to be more viscous and stick to the surface of the lactide. Therefore, it would be desirable to provide an effective method of producing a highly purified lactide substantially free of lactic acid and lactic acid oligomers, which is useful for preparing high molecular weight polylactic acid.

SUMMARY OF THE INVENTION

It is an object of the present invention to develop a process based on two reactive distillations, i.e., the first reactive distillation used for the concentration of lactic acid and preparation of lactic acid oligomers, and the second reactive distillation used for the depolymerization of the thus obtained lactic acid oligomers.

It is another object of the present invention to provide a distillation column with a vapor side-draw refluxer being connected for the purification of the crude lactide, by means of which the purified liquid lactide substantially free of lactic acid and lactic acid oligomers is obtained.

BRIEF DESCRIPTION OF THE DRAWING

FIG. 1 is a schematic representation of a preferred lactide production system in accordance with the present invention.

DETAILED DESCRIPTION OF THE PREFERRED EMBODIMENTS OF THE INVENTION

With regard to the conventional reaction sequence, water contained in lactic acid is evaporated by heating in the lactic acid concentration apparatus followed by a lactic acid condensation apparatus, wherein a lactic acid condensation (pre-polymerization) reaction is allowed to proceed for lactic acid oligomer generation. In accordance with the present invention, the two above-mentioned apparatus, i.e., lactic acid concentrator and lactic acid condensation reactor are replaced by the first reactive distillation. The expenditure on equipment and the space required for the installation of the first reactive distillation system are significantly decreased. Moreover, utilization of the first reactive distillation system has the advantage that the residence time of lactic acid is significantly reduced, minimizing the lactic acid racemization and therefore increasing the yield of target product L-lactide.

In accordance with the present invention, the first reactive distillation system preferably comprises at least a pot, a distillation column, a condenser and an evaporator. The orientation of the pot can be horizontal or vertical depending on the process conditions. The distillation column can be a conventional column or a divided wall column with a divided wall dividing the inner space of column. The condenser can be of any of the types commonly used in the chemical industry including co-current and counter-current condensers. The evaporator not only provides the energy required for the evaporation of water, but also is the place where the lactic acid condensation reaction takes place.

The aqueous solution of lactic acid can contain, for example, 0 to 50% by weight of water and 50 to 100% by weight of lactic acid, respectively. The temperature of the aqueous solution of lactic acid is preferably in the ranges of 60 to 150° C., and more preferably of 100 to 150° C.

In the first reactive distillation column, the lactic acid concentration and lactic acid condensation reaction are allowed to proceed for the generation of lactic acid oligomers. The average molecular weight of the lactic acid oligomers obtained as a result of the above lactic acid condensation reaction generally ranges from 300 to 10,000, preferably ranges from 450 to 5,000, and more preferably ranges from 600 to 2500.

The present invention is not particularly limited with regard to the type of mass transfer elements installed in the distillation column of the first reactive distillation system. Good results are obtained by using suitable mass transfer elements selected from the group consisting of trays, random packings, structured packings and any combinations thereof. It is however, structured packings are particularly suitable as mass transfer elements with the advantages of reducing the column pressure drops and liquid hold-up in the column. It is preferred that the structured packings have a specific surface area in the range of 50 to 750 $m^2/m^3$, and more preferably of in the range of 125 to 500 $m^2/m^3$.

In accordance with the present invention, the distillation column of the first reactive distillation is equipped with at least one evaporator. The evaporator can be of any of the types commonly found in the chemical industry, including, but not limited to, falling film, forced circulation, thermosiphon, short tube, long-tube vertical, long-tube horizontal and etc. However, due to its particularly reduced liquid hold-up and high heat transfer coefficient, a falling film evaporator is preferred to minimize the residence time of lactic acid in the evaporator and therefore reduce any unfavorable side-reactions, for example racemization reaction.

The distillation column and its associated evaporator of the first reactive distillation are preferably respectively mounted on top of the pot to create a single enclosed area within which lactic acid condensation and distillation take place. The aqueous solution of lactic acid is preferably continuously fed to the inlet of the distillation column, which inlet is located at a point between the upper end and lower end of the column. The reaction solution enters at the top of the falling film evaporator, flows down the long vertical tubes which comprise the heat transfer and reaction zone, and exits at the bottom of the tubes where the vapor containing stream exits the system. The vapor-liquid two-phase stream flows directly to the connected pot, wherein the vapor is disengaged from the liquid. The disengaged vapor flows upwards to the bottom of the top-mounted distillation column via the pot and the liquid from the column is recovered in the pot. To prevent liquid film breakdown inside the tubes of the falling film evaporator the vaporization of the reaction solution is generally less than 15-30% by weight. A large portion of the liquid taken from the bottom of the pot as the reaction solution is recirculated via a transfer pump to the top of the falling film evaporator for continuous lactic acid condensation while a small portion thereof is fed to the subsequent depolymerization reactor. The reaction solution is heated in general at temperatures ranging from 120 to 200° C. and preferably ranging from 150 to 180° C. under reduced pressure of 50 mbar or less and preferably 30 mbar or less.

In the process of the distillation column of the first reactive distillation, a concentration gradient is established within the column with water being enriched in the rectifying section, and the higher-boiling point components such as lactic acid and lactic acid oligomers being enriched in the stripping section. The water contained in the aqueous solution of lactic acid stream and the water generated during the lactic acid condensation is distilled off as the overhead vapor stream, which is condensed by a condenser to obtain a condensate stream consisting essentially of water. A portion of the condensate stream is preferably refluxed into the column while the other portion of the condensate stream can be discarded. Vapors that have not been condensed in the condenser is removed by the vacuum system. The high-boiling fraction consisting essentially of lactic acid and lactic acid oligomers liquefying within the column are allowed to flow back into the pot.

In accordance with the present invention, the depolymerization reactor is actually the second reactive distillation system comprising at least a pot, a distillation column, a condenser and a falling film evaporator. Similarly, in the second reactive distillation the distillation column and its associated falling film evaporator are respectively mounted directly on top of the pot to create a single enclosed area within which depolymerization and distillation take place. The mass transfer elements installed in the distillation column consist of trays, random packings, structured packings and any combinations thereof. It is however, structured packings are particularly suitable as mass transfer elements with the advantages of reducing the column pressure drops and liquid hold-up in the column. It is preferred that the structured packings have a specific surface area in the range of 50 to 750 $m^2/m^3$, and more preferably of in the range of 125 to 500 $m^2/m^3$. The condenser can be of any of the types commonly used in the chemical industry including co-current and counter-current condensers.

In the second reactive distillation catalyst such as tin dioctoate is added and mixed with the lactic acid oligomers from the first reactive distillation, which mixture as part of the reaction solution is fed to the top of the falling film evaporator, wherein lactide is generated and vaporized. The vapor-liquid two-phase stream exits at the bottom of the tubes of the falling film evaporator and flows directly to the connected pot, wherein the vapor is disengaged from the liquid. The disengaged vapor flows upwards to the bottom of the top-mounted distillation column via the pot and the liquid from the column is recovered in the pot. To prevent liquid film breakdown inside the tubes of the falling film evaporator the vaporization of the reaction solution is generally less than 15-30% by weight. A large portion of the liquid taken from the bottom of the pot as part of the reaction solution is recirculated via a transfer pump to the top of the falling film evaporator for continuous depolymerization while a small portion thereof is removed as the purge stream, which purge stream contains residues of tin catalyst and metals leached from the system. The reaction solution is heated in general at temperatures ranging from 120 to 250° C. and preferably ranging from 150 to 220° C. under reduced pressure of 100 mbar or less and preferably 20 mbar or less. An overhead low-boiling distillate stream, i.e., the crude lactide consisting of a major portion of L-lactide and some meso-lactide, lactic acid oligomer, residual water and lactic acid is formed, e.g., 60 to 99% by weight of L-lactide, 0 to 15% by weight of meso-lactide, 0 to 10% by weight of lactic acid, 0 to 12% by weight of lactic acid oligomers and 0 to 3% by weight of water. The high-boiling fraction consisting essentially of unconverted lactic acid oligomers flows back into the pot.

The crude lactide from the top-mounted distillation column of the second reactive distillation is fed to the subsequent main distillation column for the purification of L-lactide. The crude lactide is fractionated based on volatility differences between components. The relative order of decreasing volatility of the principal components in the crude lactide is water, lactic acid, meso-lactide, L-lactide and lactic acid oligomers. The less volatile components such as lactic acid oligomers, having a higher-boiling point than L-lactide, are concentrated at the bottom of the column and removed as bottoms product. The overhead product stream from the main distillation column contains a major portion of meso-lactide and a small portion of lactic acid and L-lactide. The lactide product with a high purity of L-lactide is withdrawn as the vapor side-draw from the main distillation column.

The overhead vapor stream at the top of the main distillation column is condensed by means of a condenser to obtain a condensate stream enriched in meso-lactide. Vapors that have not been condensed in the condenser are removed by the vacuum system. In order to efficiently remove other components from meso-lactide, a portion of the condensate stream is preferably refluxed into the column. The other portion of the condensate stream may be fed to an additional purification system such as a distillation, a crystallization or a combination thereof to obtain pure meso-lactide.

The liquid bottom stream concentrated in the stripping section is drawn off from the bottom of the main distillation column and subsequently divided into a bottoms product stream and a recirculation stream. The increase of lactic acid oligomers content in the bottoms product stream is observed due to the side-reactions occurring between the lactide and the residual lactic acid under the condition of a relatively high bottom temperature. The bottoms product stream is preferably refluxed to the second reactive distillation system as part of the reaction solution for the depolymerization to generate lactide.

The lactide product stream taken off as the vapor side-draw of the main distillation column is substantially free of water and lactic acid. However, it still contains a small amount of lactic acid oligomers due to the side-reactions occurring between the lactide and the residual lactic acid during the distillation. The residual lactic acid oligomers in the lactide product has a negative impact on the polymerization rates during the polymerization, resulting in a relatively low molecular weight polylactic acid.

In accordance with the present invention, the vapor side-draw stream of the above-mentioned main distillation column is fed directly to the bottom of the side-draw refluxer with a top condenser, and the bottoms product from the side-draw refluxer is refluxed back to the main distillation column. In the side-draw refluxer, L-lactide is separated from the residual lactic acid oligomers. The pure L-lactide substantially free of lactic acid and lactic acid oligomers are obtained at the top of the side-draw refluxer. The purity of L-lactide at the top of the side-draw refluxer is ensured by means of suitable methods, for example by a product analysis or an online analysis, which correspondingly influences the reflux ratio in the refluxer. The main distillation column side-draw removal rate is controlled, for example, by a temperature measurement at an appropriately sensitive point in the refluxer, which temperature measurement controls the degree of opening of a valve in the condensate line downstream of the top condenser of the refluxer. Owing to the associated influence on the liquid level and hence on the effective condensation area in this condenser, automatic regulation of the side-draw removal rate from the main distillation column is achieved.

The main distillation column with the side-draw refluxer is preferably carried out at low temperatures and reduced pressures. The pressure at the top of the main distillation column is preferably in the ranges of 3 to 25 mbar, and more preferably of 5 to 15 mbar. The pressure at the bottom of the main distillation column is preferably in the ranges of 10 to 35 mbar, more preferably of 12 to 25 mbar.

The mass transfer elements installed in the main distillation column with the side-draw refluxer consist of trays, random packings, structured packings and any combinations thereof. It is however, structured packings are particularly suitable as mass transfer elements with the advantages of reducing the column pressure drops and liquid hold-up in the column. It is preferred that the structured packings have a specific surface area in the range of 125 to 750 $m^2/m^3$, and more preferably in the range of 250 to 350 $m^2/m^3$. The condenser for the main distillation column and the side-stream column can be of any of the types commonly used in the chemical industry including co-current and counter-current condensers.

FIG. 1 schematically shows a preferred lactide production system in accordance with the present invention, which system comprises a column 2 of the first reactive distillation, a condenser 4, a pot 9, a falling film evaporator 10, a pump 12, a column 15 of the second reactive distillation, a condenser 17, a pot 22, a falling film evaporator 23, a pump 25, a main distillation column 29, a condenser 31, a pump 37, a falling film evaporator 39, a side-draw refluxer 43 and a condenser 45.

An aqueous solution of lactic acid feed is continuously fed through stream 1 to the first reactive distillation column 2. The overhead vapors consisting essentially of water are drawn off through stream 3 and subsequently condensed in the condenser 4. The condensates are divided into an overhead liquid product stream 8 distilled off from the top, and into a reflux stream 7, which is fed back to the top of the first reactive distillation column 2. The uncondensed vapors are removed through stream 5. The lactic acid and the lactic acid oligomers are concentrated at the bottom of the column 2 and flow back to the pot 9. The bottom stream 11 taken from the bottom of the pot 9 is subsequently transferred via the pump 12 and divided into a bottoms product stream 14, which stream is combined with stream 26, and a recirculation stream 13, which stream is fed to top of the falling film evaporator 10, partially vaporized and then flows to the pot 9. The vapors are disengaged from the liquid in the pot 9. The disengaged vapors flow upwards to the bottom of the column 2 and the liquid from the column is recovered in the pot 9.

The bottoms product stream 14 mixed with the depolymerization catalyst stream 28 is combined with the stream 26 and stream 41, continuously fed to the top of the falling film evaporator 23. The overhead vapors containing a large portion of lactide are drawn off through stream 16 and subsequently condensed in the condenser 17. The condensates are divided into an overhead liquid product stream 21 distilled off from the top, and into a reflux stream 20, which is fed back to the top of the second reactive distillation column 15. The uncondensed vapors are removed through stream 18. The unconverted lactic acid oligomers are concentrated at the bottom of the column 15 and flow back to the pot 22. The bottom stream 24 taken from the bottom of the pot 22 is subsequently transferred via the pump 25 and divided into a bottoms product stream 27, which stream is a purge stream, and a recirculation stream 26, which stream is fed to the top of the falling film evaporator 23, partially vaporized and then to the pot 22. The vapors are disengaged from the liquid in the pot 22. The disengaged vapors flow upwards to the bottom of the column 15 and the liquid from the column is recovered in the pot 22.

The overhead product stream 21 from the top of the second reactive distillation column 15 is fed to the main distillation column 29. The overhead vapors enriched in meso-lactide are drawn off through stream 30, which is subsequently condensed in the condenser 31. The condensates are divided into an overhead product stream 35 distilled off from the top of the main distillation column and into a reflux stream 34, which is fed back to top of the main distillation column. The uncondensed vapors are removed through stream 32. The lactic acid oligomers are concentrated at the bottom of the main distillation column 29 and drawn off as a bottom stream 36. The bottom stream 36 is subsequently divided into a bottoms product stream 41, which stream is combined with the stream 26, and a recirculation stream 38, which stream is fed to inlet of the falling film evaporator 39, partially vaporized and then flows to the bottom of the main distillation column 29 through stream 40. The vapor side-draw stream 42 has a high purity of L-lactide withdrawn at a point below the inlet stream 21 of the main distillation column 29 is fed to the bottom of the side-draw refluxer 43. The overhead vapors consisting essentially of L-lactide are drawn off through stream 44 and subsequently condensed in the condenser 45. The condensates are divided into an overhead liquid product stream 49 distilled off from the top, and into a reflux stream 48, which is fed back to the top of side-draw refluxer 43. The uncondensed vapors are removed through stream 46. The bottoms product stream 50 is refluxed to the main distillation column 29.

Subsequently, the present invention is illustrated in more details below with reference to the drawing and the examples.

EXAMPLES

Example 1

A reactive distillation of the first reactive distillation system according to an embodiment of the invention as shown in FIG. 1 was performed. The distillation column 2 has a total of 9 theoretical stages. The aqueous solution of lactic acid stream 1 (90% by weight of lactic acid) with a mass flow rate of 250 kg/h at a temperature of 110° C. was continuously fed to the distillation column 2 with the feed inlet located at the point of theoretical stage 7. Structured packings with a specific surface area of 441 $m^2/m^3$ and 250 $m^2/m^3$ were used as mass exchange elements respectively for the rectifying section and stripping section of the distillation column 2. The water was distilled off while it was generated by the dehydration of the aqueous solution of lactic acid and lactic acid condensation. The falling film evaporator 10 provided the required heat and heated the reaction solution up to a temperature of 180° C. The overhead product stream 8 with a mass flow rate of 71 kg/h, consisting of substantially pure water, was removed for further water treatment. The bottoms product stream 14 contained a major portion of lactic acid oligomers. The overhead and bottom pressure of the distillation column 2 were 22 and 27 mbar, respectively. The reflux ratio at the withdrawal point of the overhead product stream 8 was 0.5:1. Titration of the acid group content in the bottoms product showed that the lactic acid oligomers had an average number average molecular weight of 800 g/mol.

Example 2

A reactive distillation of the second reactive distillation system according to an embodiment of the invention as shown in FIG. 1 was performed. The distillation column 15 has a total of 6 theoretical stages. The bottoms product stream 14 from the first reactive distillation mixed with the catalyst (tin dioctoate) stream 28 in a static mixer (not shown in FIG. 1), with a mass flow rate of 177 kg/h and a temperature of 180° C., was combined with stream 26 and 41, which reaction solution was fed to the top of the falling film evaporator 23. Structured packings with a specific surface area of 125 $m^2/m^3$ were used as mass exchange elements for the distillation column 15.

The lactide was distilled off while it was generated by the depolymerization of the lactic acid oligomers in the falling film evaporator 23, which evaporator heated the reaction solution up to a temperature of 215° C. The overhead product stream 21 with a mass flow rate of 172 kg/h, greater than 85% by weight of L-lactide, was removed for further purification. The bottoms product stream 27 was removed as the purge stream. The overhead and bottom pressure of the distillation column 15 were 7 and 12 mbar, respectively. The reflux ratio at the withdrawal point of the overhead product stream 21 was 0.3:1.

Example 3

A distillation of the main distillation with the side-draw refluxer according to an embodiment of the invention as shown in FIG. 1 was performed. Structured packings with a specific surface area of 345 $m^2/m^3$ were used as mass exchange elements for the two columns. The main distillation column 29 has a total of 35 theoretical stages and the side-draw refluxer 43 has a total of 6 theoretical stages. The overhead product stream 21 from the second reactive distillation with a mass flow rate of 3550 kg/h at a temperature of 107° C. was continuously fed to the main distillation column 29 with the feed inlet located at the point of theoretical stage 9. The vapor side-draw stream 42 from the main distillation column 29 was taken off at the point of theoretical stage 33 and fed to the bottom of the side-draw refluxer 43. The bottoms product stream 50 from the side-draw refluxer 43 is refluxed back to the main distillation column 29 with the feed inlet located at the point of theoretical stage 33. In the main distillation column 29, the overhead product stream 35 was enriched with meso-lactide and the bottoms product stream 41 contained a major portion of lactic acid oligomers. The overhead product stream 49 from the side-draw refluxer 43 was virtually pure L-lactide and used for subsequent polymerization. The overhead and bottom pressure of the main distillation column 29 were 8 and 16 mbar, respectively. The reflux ratio at the withdrawal point of the overhead product stream 35 was 5.5:1. The energy consumption was 1.2 MW for the main distillation column 29. The compositions of different streams were tabulated in the following table.

| | | Feed stream 21 | Overhead product stream 35 | Bottoms product stream 41 | Overhead product stream 49 |
|---|---|---|---|---|---|
| Water | wt. % | 0.96 | 0.44 | 0 | 0 |
| Lactic acid | wt. % | 2.40 | 16.53 | 0 | 0 |
| Lactyl lactate | wt. % | 0.19 | 1.31 | 0 | 0 |
| Meso-lactide | wt. % | 10.16 | 66.49 | 0.02 | 0.23 |
| L-lactide (incl. D-lactide) | wt. % | 85.33 | 15.24 | 20.27 | 99.76 |
| Lactic acid oligomers | wt. % | 0.96 | 0 | 79.71 | 0.01 |

Comparative Example 3

A distillation in a distillation column with a vapor side-draw for purification of lactide was performed. Structured packings with a specific surface area of 345 $m^2/m^3$ were used as mass exchange elements in the column. The column had the same number of theoretical stages as the main distillation column 29 described in Example 3, i.e., a total of 35 theoretical stages. The overhead product stream 21 with a mass flow rate of 3550 kg/h at a temperature of 107° C. was continuously fed to the distillation column with the feed inlet located at the point of theoretical stage 9. The vapor side-draw stream from the distillation column was taken off at the point of theoretical stage 33 for further purification or polymerization. The overhead and bottom pressure of the distillation column were 8 and 16 mbar, respectively. The reflux ratio at the withdrawal point of the overhead product stream was 5.5:1. The energy consumption was 1.2 MW for the distillation column with a vapor side-draw. The compositions of different streams were tabulated in the following table.

| | | Feed Stream 21 | Overhead product stream | Bottoms product stream | Vapor side-draw product stream |
|---|---|---|---|---|---|
| Water | wt. % | 0.96 | 0.43 | 0 | 0 |
| Lactic acid | wt. % | 2.40 | 16.42 | 0 | 0 |
| Lactyl lactate | wt. % | 0.19 | 1.30 | 0 | 0 |
| Meso-lactide | wt. % | 10.13 | 66.38 | 0.01 | 0.21 |
| L-lactide (incl. D-lactide) | wt. % | 85.36 | 15.47 | 20.21 | 99.56 |
| Lactic acid oligomers | wt. % | 0.96 | 0 | 79.77 | 0.23 |

As described in the above examples according to the present invention, the virtually pure L-lactide is obtained by the means of two reactive distillations followed by a main distillation column with a side-draw refluxer. The process for the production of L-lactide of the present invention has the advantages that the investment cost is reduced and a highly pure L-lactide substantially free of lactic acid oligomers is produced, which L-lactide can be polymerized to high molecular weight polylactic acid without further purification. The process of the present invention will be also applicable to the production of pure D-lactide if the aqueous solution of lactic acid containing a large portion of (R)-lactic acid is used as the raw material.

What is claimed is:

1. A continuous process for production of lactide from an aqueous solution of lactic acid, the process comprising:

a) generating lactic acid oligomers in a first enclosed system comprising a first pot, a first distillation column mounted on top of the first pot, and a first falling film evaporator mounted on top of the first pot, comprising:

i) feeding the aqueous solution of lactic acid to the first distillation column through a feed inlet located at a point between an upper end and a lower end of the first distillation column;

ii) withdrawing a liquid from a bottom of the first pot, wherein a large portion of the withdrawn liquid forms a reaction solution and a small portion of the withdrawn liquid is fed to step b);

iii) feeding the reaction solution to a top of the first falling film evaporator, allowing the reaction solution to flow down a plurality of tubes that define a heat-transfer and reaction zone, and discharging from a bottom of the tubes a vapor-liquid two-phase stream that flows directly to the first pot, wherein vapor is disengaged from liquid in the first pot;

iv) flowing the disengaged vapor upward from the first pot to a bottom of the first distillation column, and recovering in the first pot a liquid from the first distillation column; and v) distilling off water as an overhead vapor stream from the first distillation column, and allowing a high-boiling fraction consisting of lactic acid and lactic acid oligomers liquefying within the first distillation column to flow back into the first pot; and b) generating crude lactide in a second enclosed system comprising a second pot, a second distillation column mounted on top of the second pot, and a second falling film evaporator mounted on top of the second pot from the lactic acid oligomers generated in the step a), comprising:

i) feeding the small portion of the withdrawn liquid from step a) ii), comprising the lactic acid oligomers, to the second enclosed system;

ii) withdrawing a liquid from a bottom of the second pot and combining at least a portion thereof with the small portion of the withdrawn liquid from the step a) ii) to form a depolymerization reaction solution;

iii) feeding the depolymerization reaction solution to a top of the second falling film evaporator for continuous depolymerization;

iv) discharging from a bottom of tubes of the second falling film evaporator a vapor-liquid two-phase stream that flows directly to the second pot, wherein vapor is disengaged from liquid in the second pot;

v) flowing the disengaged vapor upward from the second pot to a bottom of the second distillation column, and recovering in the second pot a liquid from the second distillation column; and vi) forming crude lactide as an overhead low-boiling distillate stream comprising a major portion of L-lactide and some meso-lactide, lactic acid oligomer, residual water, and lactic acid, and allowing a high-boiling fraction comprising unconverted lactic acid oligomers to flow back into the second pot.

2. The process of claim 1, wherein the aqueous solution of lactic acid comprises 50% to less than 100% by weight of lactic acid.

3. The process of claim 1, wherein the first pot of step a) and the second pot of step b) are arranged horizontally or vertically.

* * * * *